United States Patent
Dobrean

(10) Patent No.: US 10,949,501 B2
(45) Date of Patent: Mar. 16, 2021

(54) SYSTEM AND METHOD FOR COMPILING MEDICAL DOSSIER

(71) Applicant: AGFA HEALTHCARE, Mortsel (BE)

(72) Inventor: George M. Dobrean, Kitchener (CA)

(73) Assignee: AGFA HEALTHCARE, Mortsel (BE)

( * ) Notice: Subject to any disclaimer, the term of this patent is extended or adjusted under 35 U.S.C. 154(b) by 1239 days.

(21) Appl. No.: 14/845,832

(22) Filed: Sep. 4, 2015

(65) Prior Publication Data

US 2017/0068780 A1 Mar. 9, 2017

(51) Int. Cl.
| | |
|---|---|
| G16H 30/20 | (2018.01) |
| G16H 30/40 | (2018.01) |
| G06F 19/00 | (2018.01) |
| G16H 10/60 | (2018.01) |
| G16H 15/00 | (2018.01) |
| A61B 8/08 | (2006.01) |

(52) U.S. Cl.
CPC .............. G06F 19/321 (2013.01); A61B 8/52 (2013.01); G16H 10/60 (2018.01); G16H 15/00 (2018.01); G16H 30/20 (2018.01); G16H 30/40 (2018.01)

(58) Field of Classification Search
CPC ...... G06F 19/00; G06F 19/321; G06F 19/325; G06F 19/328; G16H 10/60; G16H 50/20; G16H 10/20; G16H 50/50; G16H 50/30; G16H 50/70; G16H 15/00; G16H 20/10; G16H 40/63; G16H 40/67; G16H 40/20; G06Q 50/22; G06Q 10/0637; G06Q 10/0639; G06Q 10/10; G06Q 10/00; G06Q 20/10; G06Q 20/18; G06Q 20/342; G06Q 30/0215; G06Q 50/01; G06Q 50/24

USPC .............................................................. 705/3
See application file for complete search history.

(56) References Cited

U.S. PATENT DOCUMENTS

| | | | |
|---|---|---|---|
| 7,395,215 B2 | 7/2008 | Grushka | |
| 8,180,654 B2 | 5/2012 | Berkman et al. | |
| 8,321,241 B1 | 11/2012 | Mansour et al. | |
| 2005/0144039 A1* | 6/2005 | Tamblyn | G06F 19/328 705/2 |
| 2006/0080140 A1 | 4/2006 | Buttner et al. | |
| 2007/0165049 A1 | 7/2007 | Murawski et al. | |
| 2010/0070300 A1 | 3/2010 | Anderson et al. | |
| 2010/0198619 A1* | 8/2010 | Whelchel | G06Q 10/06 705/3 |

(Continued)

FOREIGN PATENT DOCUMENTS

WO 2010148127 A2 12/2010

OTHER PUBLICATIONS

International Search Report and Written Opinion dated Dec. 1, 2016 in corresponding International Patent Application No. PCT/EP2016/069922.

(Continued)

*Primary Examiner* — Trang T Nguyen
(74) *Attorney, Agent, or Firm* — Lewis Rice LLC

(57) ABSTRACT

A system and method for compiling a clinically logical medical dossier for a patient. A list of medical conditions can be determined for the patient. A plurality of medical imaging records for the patient can be identified, and each record can be assigned to one of the conditions. A timeline of condition-specific imaging records can then be generated for each condition. A condition can be selected and the timeline of condition-specific imaging records for the selected condition can then be displayed.

17 Claims, 7 Drawing Sheets

(56) References Cited

U.S. PATENT DOCUMENTS

| | | | |
|---|---|---|---|
| 2011/0022413 A1* | 1/2011 | Markessini | G06Q 10/10 |
| | | | 705/3 |
| 2011/0145012 A1 | 6/2011 | Nightingale et al. | |
| 2012/0113239 A1 | 5/2012 | Krupnik et al. | |
| 2012/0131507 A1 | 5/2012 | Sparandara et al. | |
| 2013/0110543 A1* | 5/2013 | Leighow | G06Q 50/24 |
| | | | 705/3 |
| 2013/0290024 A1 | 10/2013 | Kawanaka et al. | |
| 2013/0290025 A1 | 10/2013 | Halderman | |
| 2014/0278528 A1 | 9/2014 | Simha et al. | |
| 2014/0350961 A1 | 11/2014 | Crurka et al. | |
| 2015/0066539 A1* | 3/2015 | Sheffer | G06Q 50/22 |
| | | | 705/3 |
| 2015/0089365 A1* | 3/2015 | Zhao | G06F 19/321 |
| | | | 715/708 |

OTHER PUBLICATIONS

International Preliminary Report on Patentability dated Mar. 6, 2018 in corresponding International Patent Application No. PCT/EP2016/069922.

* cited by examiner

SYSTEM AND METHOD FOR COMPILING MEDICAL DOSSIER

FIELD

The embodiments described herein relate to a system and method for compiling a medical dossier and more particularly a system and method for generating a timeline of medical imaging records.

BACKGROUND

When a patient sees a physician or is admitted to hospital, it is important to have a complete patient history available to the physician and other medical professionals. At the same time, it is also important that a diagnosing physician be able to easily identify the specific imaging records in the patient's medical history that are pertinent to the current condition(s) for which treatment is being sought.

Today's patients tend to have increasingly long and complex medical histories. People are living longer and previously deadly diseases and conditions are being transformed into manageable conditions. As a result, patients tend to have a greater number of ongoing medical conditions. The increased number of ongoing medical conditions means patient histories are becoming bloated with imaging records related to each of the various conditions. This can make it difficult for attending physicians to identify relevant medical imaging records when treating a patient.

Electronic medical records or electronic patient records may ensure that doctors have access to complete (or more complete) medical histories for a patient—even if they are located remote from the patient's usual care facility. As well, electronic medical record systems allow a patient's records to be remotely updated and synchronized across multiple medical facilities. While electronic patient record systems may streamline compiling and managing patient medical histories, these patient histories are still bloated. In addition, some medical imaging records such as medical images can be extremely large in size. Transferring the entirety of a patient's medical imaging records from a centralized database to the medical facility where the patient is being seen can be slow and may consume limited network resources.

A system and method for compiling a medical imaging dossier that allows a doctor to easily identify and review relevant medical imaging records for a patient may alleviate some of these issues. Such a system may also reduce the amount of data that must be transferred from central databases to clinician workstations when the patient is being diagnosed or treated.

SUMMARY

In accordance with an aspect of an embodiment of the invention, there is provided a method for compiling a medical dossier. The method includes determining a condition list for a patient, where the condition list has a plurality of condition markers with each condition marker representing a medical condition; identifying a plurality of medical imaging records for the patient, with each medical imaging record having an imaging date; determining at least one condition-specific imaging record for each condition marker by assigning each imaging record to one of the condition markers in the condition list; generating a timeline of condition-specific imaging records for each condition marker in the condition list using the imaging date of the condition-specific imaging records for that condition marker; receiving a selection of a first condition marker in the condition list; and displaying the timeline of the condition-specific imaging records for the first condition marker.

In some embodiments, the timeline for a particular condition marker can be generated to include an image record identifier for each condition-specific imaging record for that particular condition marker. In some embodiments, the condition-specific imaging records for the particular condition marker can include at least one medical image; and for each medical image, the image record identifier can be a thumbnail image of the medical image.

In some embodiments, the image record identifier for each condition-specific imaging record can include a record type identifier.

In some embodiments, the method may further include receiving a selection of a second condition marker from the condition list; and displaying the timeline of the condition-specific imaging records for the second condition marker.

In some embodiments, the method may further include generating a combined timeline of the condition-specific imaging records for the first condition marker and the condition-specific imaging records for the second condition marker. The combined timeline can include a first condition identifier associated with each of the condition-specific imaging records for the first condition marker and a second condition identifier associated with each of the condition-specific imaging records for the second condition marker, where the second condition identifier being different than the first condition identifier.

In some embodiments, for at least one imaging record, that imaging record can be assigned to the condition marker by determining if a codified condition marker is present in that imaging record, where the codified condition marker corresponds to a standard encoding of a particular condition marker in the condition list; and if the codified condition marker is present, assigning that imaging record to the particular condition marker.

In some embodiments, the method may further include identifying the condition marker using natural language processing if the codified condition marker is not present; and assigning that imaging record to the identified condition marker.

In some embodiments, the method may further include, if the codified condition marker is not present, displaying each of the at least one imaging record in the user interface; receiving a user-selected condition marker from the user interface for each of the at least one imaging record; and assigning each imaging record in the at least one imaging record to the user-selected condition marker for that imaging record.

In some embodiments, the method may further comprise displaying the condition list on a user interface; and receiving the selection of the first condition marker from the user interface in response to the displayed condition list.

In accordance with an embodiment of the invention, there is provided a system for compiling a medical dossier. The system includes a database memory for storing a plurality of medical records, a user interface having a display device and a user input device, and a processor coupled to the database memory and the user interface. The processor can be configured to determine a condition list for a patient, the condition list including a plurality of condition markers, each condition marker representing a medical condition; identify a plurality of medical imaging records for the patient from the medical records stored in the database memory, each medical imaging record having an imaging date; determine at least one condition-specific imaging record for each condition marker by assigning each imaging record to one of the condition markers in the condition list; generate a timeline of condition-specific imaging records for each condition marker in the condition list using the imaging date of the condition-specific imaging records for that condition marker; receive a selection of a first condition marker in the condition list from the user input device; and display the timeline of the condition-specific imaging records for the first condition marker using the display device.

In some embodiments, the processor can be configured to generate the timeline for a particular condition marker to include an image record identifier for each condition-specific imaging record for that particular condition marker.

In some embodiments, the condition-specific imaging records for a particular condition marker include at least one medical image, and the processor can be further configured to, for each medical image, display a thumbnail image of the medical image as the image record identifier for that medical image using the display device.

In some embodiments, the image record identifier for each condition-specific imaging record can include a record type identifier.

In some embodiments, the processor can be further configured to receive a selection of a second condition marker in the condition list from the user input device, and display the timeline of the condition-specific imaging records for the second condition marker using the display device.

In some embodiments, the processor can be further configured to generate a combined timeline of the condition-specific imaging records for the first condition marker and the condition-specific imaging records for the second condition marker, the combined timeline including a first condition identifier associated with each of the condition-specific imaging records for the first condition marker and a second condition identifier associated with each of the condition-specific imaging records for the second condition marker, the second condition identifier being different than the first condition identifier.

In some embodiments, for at least one imaging record, the processor can be configured to assign that imaging record to the condition marker by determining if a codified condition marker is present in that imaging record, the codified condition marker corresponding to a standard encoding of a particular condition marker in the condition list; and if the codified condition marker is present, assigning that imaging record to the particular condition marker.

In some embodiments, the processor can be further configured to identify the condition marker using natural language processing if the codified condition marker is not present; and assign that imaging record to the identified condition marker.

In some embodiments, the processor can be further configured to, if the codified condition marker is not present, display each of the at least one imaging record using the display device; receive a user-selected condition marker from the user input device for each of the at least one imaging record; and assign each imaging record in the at least one imaging record to the user-selected condition marker for that imaging record.

In some embodiments, the processor the processor can be further configured to display the condition list using the display device; and receive the selection of the first condition marker from the user input device in response to the displayed condition list.

Further aspects and advantages of the embodiments described herein will appear from the following description taken together with the accompanying drawings.

DRAWINGS

For a better understanding of the embodiments described herein and to show more clearly how they may be carried into effect, reference will now be made, by way of example only, to the accompanying drawings which show at least one exemplary embodiment, and in which.

Figure 1:
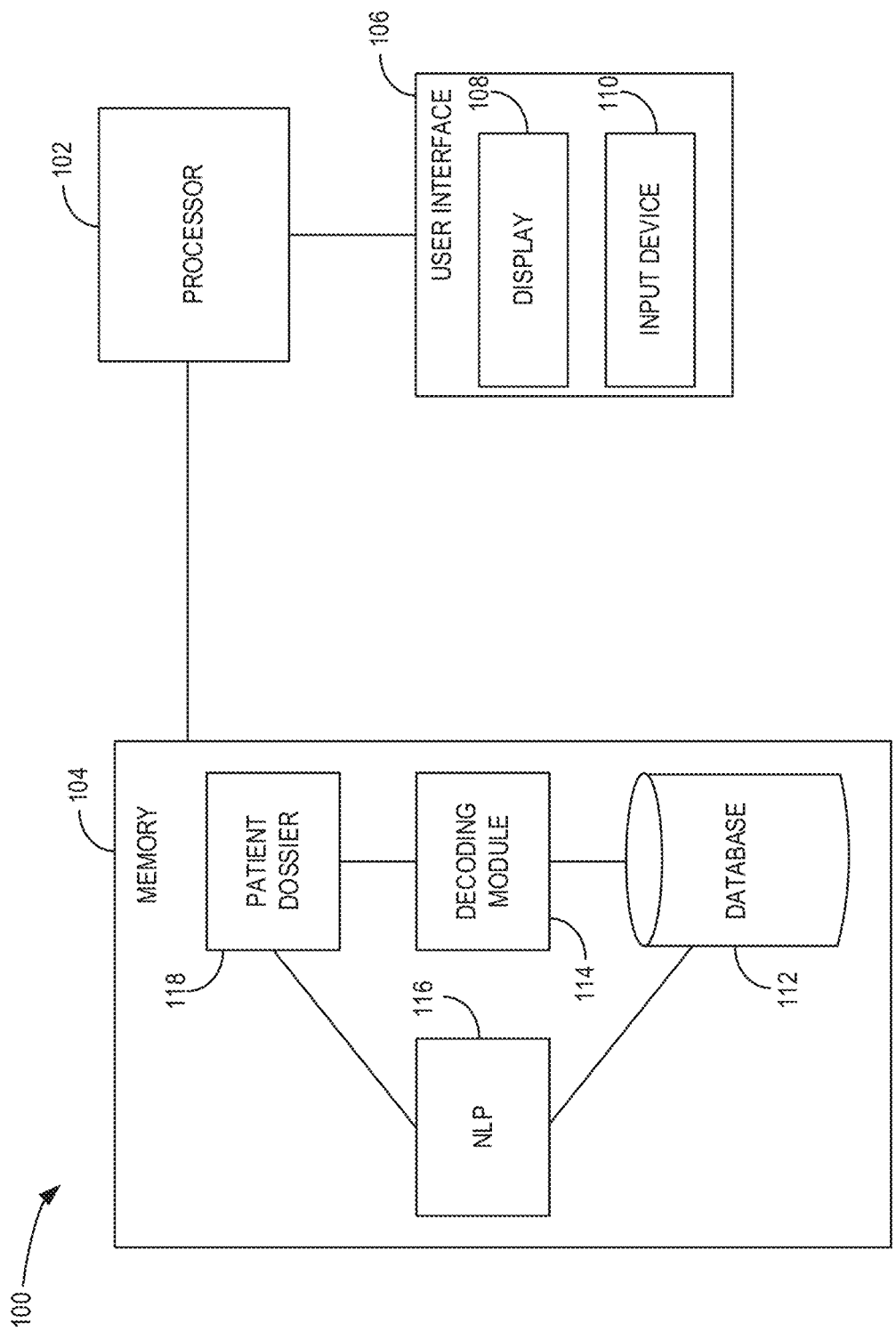
FIG. 1 is a block diagram of a system for compiling a medical dossier.

The skilled person in the art will understand that the drawings, described below, are for illustration purposes only. The drawings are not intended to limit the scope of the applicants' teachings in any way. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein. Where considered appropriate, for simplicity and clarity of illustration, reference numerals may be repeated among the figures to indicate corresponding or analogous elements or steps.

The embodiments of the systems and methods described herein may be implemented in hardware or software, or a combination of both. However, preferably, these embodiments are implemented in computer programs executing on programmable computers each comprising at least one module component which comprises at least one processor (e.g. a microprocessor), a data storage system (including volatile and non-volatile memory and/or storage elements), at least one input device, and at least one output device. For example and without limitation, the programmable computers (referred to below as computing devices) may be a personal computer, laptop, personal data assistant, and cellular telephone, smart-phone device, tablet computer, and/or wireless device. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The subject system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The embodiments described herein provide systems and methods for compiling a medical dossier for a patient. The embodiments described herein can provide a clinician with a dossier of medical imaging records for a patient that is both comprehensive and easily navigable. The patient's medical imaging records can be managed and organized using conditions markers representing a patient's medical conditions or diseases. The patient's dossier can then be presented to a clinician in a streamlined and segregated manner that allows the clinician to rapidly identify and assess relevant imaging records.

In general, the systems and methods described herein are configured to provide a medical professional with a clinically logical medical dossier. That is, the systems and methods described herein may effectively automate some aspects of clinical reasoning that would heretofore have been applied by a clinician. In the past, when reviewing data in a patient's medical records, a clinician may apply clinical logic to only consider records pertaining to the same medical condition. However, the clinician is still required to review and sort through the patient's entire medical record and determine which records are pertinent to the medical condition that is currently of concern. As well, in such systems the entirety of the patient's medical records must still be transmitted to a workstation at the physician's location. The present application provides systems and methods that can generate a clinically logical medical dossier by grouping a patient's medical imaging records based on medical condition.

When a patient with chronic heart disease is admitted to the hospital with a cough, the patient isn't being admitted because of their chronic heart disease. At the same time, it is incorrect to say the heart disease is part of their past medical history. The chronic heart disease is an ongoing, usually lifelong disease requiring constant management. Thus, medical imaging records related to the patient's chronic heart disease should maintain relevance to the patient's ongoing conditions. At the same time, it is inefficient for a physician to scour through all the medical imaging records related to the patient's ongoing conditions just to identify the imaging records relevant to the condition being treated.

In embodiments described herein, an actively managed condition list can be integrated into a patient's medical dossier. The condition list can include condition markers corresponding to the patient's ongoing medical/clinical conditions. The chronic heart disease mentioned above may be an example of one condition marker found on a patient's condition list. Each medical imaging record for the patient can be associated with one of the condition markers. When the physician is attending to the patient, the physician can use the association between condition markers and medical imaging records to reduce the number of medical imaging records they have to review.

The embodiments described herein can enable relevant medical imaging data to be quickly identified and compiled. This may reduce the amount of imaging data that needs to be transmitted from a centralized database to an end-user clinician workstation. Rather than transmitting the entirety of a patient's medical records, in some cases only imaging records related to condition markers selected by a clinician need be transmitted. Thus, relevant medical imaging records can be delivered to a clinician more rapidly and without unduly consuming network resources.

The medical imaging records that are delivered to a clinician workstation can be presented in a less cluttered format allowing the clinician to rapidly sort and analyze relevant medical imaging records. A less cluttered presentation of medical imaging records may lead to increased efficiency on the part of the diagnosing clinician, as they are no longer required to comb through irrelevant records to find the medical imaging records of interest. As well, the more focused selection of medical imaging records may reduce the risk of relevant imaging records being overlooked by highlighting the records relevant to the condition being analyzed or diagnosed.

For example, consider a patient with multiple sclerosis (MS). If a clinician wants to review the course of treatment for MS over the last ten years, typically the clinician would have to sift back through almost every prior medical imaging record to identify ones where MS was discussed or mentioned. The clinician may have to open and review numerous irrelevant imaging records to determine that they are not relevant. This is a very time-consuming task and prone to error, as some relevant records may be accidentally overlooked. Assigning each imaging record to a condition marker in a condition list allows each imaging record to be assigned specific relevance for any given condition marker the clinician is considering.

In some embodiments, a user can retrieve every imaging record relating to MS for this patient with a single action (e.g. a click), whether from an emergency department, ambulatory clinic, radiological department etc. Thus, a clinician is able to perform a focused review of imaging medical imaging records for a large time-period, without having to manually filter through numerous irrelevant imaging records. As well, the task can be performed rapidly from a remote workstation, without having to transfer the entirety of the patient's imaging records for the time period of interest.

Referring now to FIG. 1, shown therein is a block diagram of a system 100 for compiling a medical dossier. System 100 includes a processor 102 coupled to a memory 104 and a user interface 106.

In some cases, the processor 102 and user interface 106 may be provided together as a clinician workstation. The clinician workstation may be coupled to a remote database workstation housing the memory 104 over a network, such as the Internet and/or various types of telecommunication networks. Alternatively, the processor 102, memory 104, and user interface 106 may be contained in a medical imaging records workstation.

The memory 104 can include a database 112 for storing a plurality of medical imaging records. The database 112 can store medical imaging records for one or more patients. Memory 104 can also have stored thereon software components such as a decoding module 114 and a natural language processing (NLP) module 116.

The programs stored in the decoding module 114 and the NLP module 116 can be operated to compile a patient dossier 118 for a particular patient. The patient dossier 118 can be compiled by decoding or extracting condition markers from the medical imaging records stored in the database 112. The patient dossier 118 can include a condition list including a plurality of condition markers representing medical conditions for a patient. The processor 102 or a processor on a database workstation may be configured to compile a plurality of patient dossiers 118, with one patient dossier for each different patient. The patient dossiers 118 can also be stored in memory 104.

The patient dossier 118 can also segregate the medical imaging records stored in database 112 into condition-specific imaging records. The patient dossier 118 may also include a timeline of condition-specific imaging records for each of the condition markers in the condition list.

The user interface 106 is provided to allow a user compiling, managing or reviewing a patient's medical records to interact with the medical dossier compilation system 100. A user may be a medical professional such as a doctor, dentist, physician, etc. The user interface 106 can include a display device 108 and an input device 110. The input device 110 may be any device that allows the user to send commands to the medical dossier compilation system 100. The input device may be, but not limited to, a keyboard, a stylus, a mouse, a dictation device, a voice recognition system, or a motion detection sensor. Display device 108 may include any type of device for presenting visual information. For example, display device 108 may be a computer monitor, a flat-screen display, a projector or a display panel.

It should be understood that the medical dossier compilation system 100 may be implemented in hardware or software or a combination of both. Specifically, various modules of medical dossier compilation system 100 are preferably implemented in computer programs executing on programmable computers, each comprising at least one processor, a data storage system, at least one input device and at least one output device. Without limitation, the programmable computers may be a mainframe computer, server, personal computer, laptop, personal data assistant, cellular telephone, smartphone or tablet device.

In an exemplary implementation, the medical dossier compilation system 100 is implemented in software and installed on the hard drive of any suitable client workstation, such that the client workstation interoperates with a database workstation in a client-server configuration. The database workstation may store the database 112 and patient dossier 118 for a particular patient. The database workstation may be accessed by the processor 102 of the client workstation to retrieve a condition list and condition-specific imaging records for a patient. In some cases, the NLP module 116 and decoding module 114 may be stored on the database workstation and the processor 102 of the client workstation can access these software modules remotely. Alternatively, the NLP module 116 and decoding module 114 may be installed locally on the clinician workstation to allow new medical imaging records to be analyzed locally at the clinician workstation.

Rather than transferring the entirety of a patient's medical dossier to the client workstation, the processor 102 may receive a selection of one or more specific condition markers from the user input device 110. For instance, the processor 102 may access the database 112 to retrieve a condition list for a particular patient. The condition list may be displayed to a clinician on display device 108. The clinician can then select a condition marker from the displayed condition list using the input device 110. Alternatively, the clinician may operate the input device 110 to perform a search of the condition list retrieved by the processor 102. The clinician may then select a condition marker from the retrieved search results.

Once a condition marker has been selected, the processor 102 may retrieve the timeline of condition-specific imaging records for that condition marker. Rather than transmitting all medical imaging records to the client workstation, the medical dossier compilation system 100 may limit the transmission to only relevant imaging records identified by the selected condition marker. As a result, the clinician may receive relevant imaging records more rapidly, especially if the clinician's workstation is located remotely from the database 112. In addition, less data needs to be transmitted over the network between the database 112 and the clinician's workstation, thereby freeing up additional network bandwidth for other users.

Figure 2:
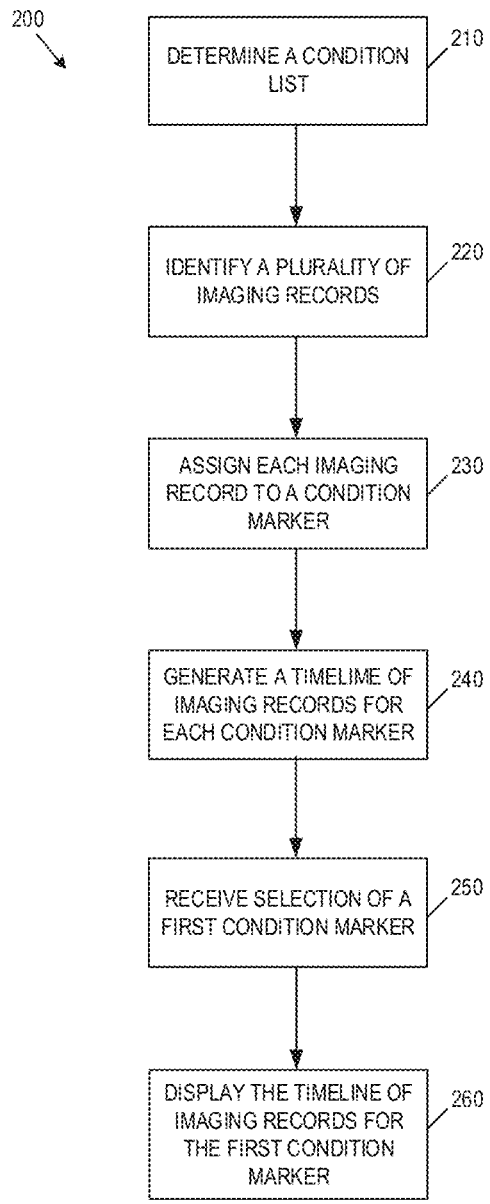
FIG. 2 is a flowchart diagram illustrating the steps of a method compiling a medical dossier within the system of FIG. 1.

Referring now to FIG. 2, shown therein is a flowchart illustrating an example method 200 for compiling a medical dossier. Method 200 is an example of a method that may be performed by a system such as system 100.

At 210, the processor 102 can determine a condition list for a patient. The condition list typically includes a plurality of condition markers with each condition marker representing a medical condition. The condition list will typically be determined individually for each patient.

In general, a condition list is a list of medical conditions such as illnesses, injuries, and other factors that may affect the health of an individual patient. The processor 102 may determine the condition list for a particular patient based on medical records stored in database 112, such as medical imaging records for that patient. In some instances, condition markers may also be identified based on input received from user input device 110. For instance, a clinician may indicate a particular condition affecting the patient.

When the patient is diagnosed or treated for a new condition, a corresponding condition marker can be added to the condition list for that patient. In some cases, the condition marker can be added to the condition list automatically, based on analysis of the patient's medical records. In other cases, the condition marker may be added to the condition list based on input from user input device 110. Treating clinicians can also review the condition list for a particular patient to add new condition markers and enter updates/corrections as required. For instance, a treating clinician may determine that a particular condition was incorrectly diagnosed and may operate user input device 110 to change the condition marker to a different condition marker representing the correct diagnosis.

In some cases, e.g. if a condition has been resolved and no longer affects the health of the patient, the associated condition marker may be removed from the condition list for that patient. This can further reduce the clutter in an imaging record condition list when a clinician wants to identify medical imaging records associated with the condition being diagnosed or treated.

Condition markers for resolved or past conditions no longer affecting a patient can still be stored in the patient dossier 118. In some cases, a separate list of historical condition markers may be maintained for conditions that are no longer affecting a patient. These markers may be excluded from the patient's condition list, but can still provide a clinician with a streamlined way to review historical conditions if desired. Maintaining medical imaging records assigned to condition markers for both ongoing and historical conditions may provide a helpful resource for research studies, quality measures, and other secondary data-reporting requirements, so that the patient dossier 118 can be easily mined for records relevant to a condition of interest.

The patient dossier 118 may also store additional details related to each condition marker such as the time of occurrence/onset, the time of identification, chronicity (chronic, acute/self-limiting, etc.), and resolution among others. As well, when changes are made to aspects of the patient dossier 118, such as the condition list, the source (i.e. clinician or system that performed the update), date and time of all updates can be captured and logged. This data may subsequently be useful in identifying the source of errors in managing the patient's dossier.

In some cases, the condition markers may correspond to codified condition markers for particular medical conditions. For example, the condition markers may correspond to codified markers defined using national/international standards (e.g. HL7, DICOM), and/or they may be codified based on known significant medical diagnoses and conditions specific to an institution (e.g. diagnostic codes). As such, identification of condition markers in a patient's medical imaging records or associated metadata may be achieved by automatically identifying codified condition markers using the decoding module 114. Alternatively, condition markers may be identified by analyzing the free text contents of the medical imaging records, for example using natural language processing module 116.

At 220, the processor 102 can identify a plurality of medical imaging records for the patient. Medical imaging records generally refer to medical imaging data generated by radiological and other imaging procedures (e.g. ultrasound images, CT scans, MRIs X-rays etc.) as well as associated medical reports and other types of related attachments such as comments, voice clips, hyperlinks etc.

The medical imaging records can be stored in database 112. In general, each medical imaging record will have an imaging date indicating the date on which the image was acquired. In some cases, the imaging date for each medical imaging record may be determined by analyzing the content of the medical imaging record, or by analyzing metadata associated with the medical imaging record. Some medical imaging records can be quite large in size, particularly as the resolution of imaging procedures continues to improve. As a result, it may be undesirable to have to transfer medical imaging records to a clinician workstation unless they are relevant or necessary.

At 230, the processor 102 can determine at least one condition-specific imaging record for each condition marker by assigning each imaging record to one of the condition markers in the condition list. For instance, a breast mammogram imaging record may be assigned to a breast cancer condition marker, while a throat endoscopy imaging record may be assigned to a hoarse voice condition marker. In general, the imaging records can be assigned to a condition marker in the same manner as above, where condition markers can be automatically determined using the decoding module 114 and/or NLP module 116.

While steps 210-230 have been shown and described above as separate steps, it should be apparent that these steps may be performed concurrently. For instance, when a medical imaging record is identified for a patient and associated with a condition marker not currently in the condition list for a patient, that condition marker can be added to the condition list and the medical imaging record can be concurrently assigned to that new condition marker. In general, the condition list determined at 210 is defined to include only condition markers that represent conditions the patient has been identified to have.

In some cases, for at least one imaging record, the processor 102 can determine if a codified condition marker is present in that imaging record using decoding module 114. The codified condition marker may correspond to a standard encoding of a particular condition marker in the condition list. For example, the codified condition marker may be codified using a medical standard such as an HL7 standard (FHIR® or previous versions) or DICOM standard. The decoding module 114 can be configured to translate the identified condition markers for a plurality of standard encodings into the condition markers in the patient's condition list. If the codified condition marker is present, the processor 102 can assign that imaging record to the particular condition marker corresponding to the codified condition marker (see e.g. FIG. 4A below).

In some cases, if a codified condition marker is not present, the processor 102 can identify the condition marker for an imaging record using the natural language processing module 116 (see e.g. natural language processing module 720 in FIG. 4B below). Natural language processing module 720 may implement any of a number of natural language processing techniques. Once a condition marker is identified, the processor 102 can then assign that imaging record to the identified condition marker.

In some cases, if the codified condition marker is not present the processor 102 may display the imaging record using the display device 110. For example, the imaging record may be displayed in a waiting for placement queue (see e.g. FIGS. 3B and 3C). The processor 102 can receive a user-selected condition marker from the user input device 110 for each of the unassigned imaging records displayed. The processor 102 can then assign each imaging record to the user-selected condition marker for that imaging record. In some cases, a user may also re-assign an imaging record to a different condition marker using the input device 110. For instance, if the clinician determines that a condition marker reflects an incorrect diagnosis, all medical imaging records associated with that condition markers may be re-assigned to the new diagnosed condition indicated by the physician. Alternatively, the clinician may simply determine that a medical imaging record should be assigned to a different condition marker for the patient.

At 240, the processor 102 can generate a timeline of condition-specific imaging records for each condition marker in the condition list using the imaging date of the condition-specific imaging records for that condition marker. The timelines of condition-specific imaging records can include each imaging record associated with a particular condition marker ordered chronologically. Such timelines can emphasize to a physician the most recent imaging records for a patient, as well as indicate the progress of the patient's imaging records over time for the condition marker. The timelines of condition-specific imaging records can be stored in the patient dossier 118 for each patient.

At 250, the processor 102 may receive a selection of a first condition marker in the condition list from the user input device 110. In some cases, the condition list may be displayed using the display device 108 of the user interface 106. For example, a drop-down list of condition markers in the condition list for a patient may be presented to a user on the display device 108. A user may then select the first condition marker from the displayed condition list using the input device 110. Alternatively, a user may use a search function to identify potentially relevant condition markers, and select the first condition marker from among the search results.

At 260, the processor 102 can display the timeline of the condition-specific imaging records for the first condition marker selected at 250 using the display device 108. For instance, the processor 102 may request the condition-specific imaging records for the first condition marker from a database workstation storing the patient dossier 118. The timeline can then be transmitted to a client workstation to be displayed to a user by display device 108.

In some cases, the timeline for a particular condition marker can be generated to include an image record identifier for each condition-specific imaging record for that particular condition marker. The image record identifier may include information about the imaging record, such as a record type identifier, a record date, a preview of the imaging record etc.

For instance, where the condition-specific imaging records for the particular condition marker include at least one medical image, the processor 102 may generate the image record identifier for each medical image as a thumbnail image of the medical image. This may provide a clinician with a rapid visual indication of whether the medical imaging record is relevant to the particular condition being assessed. Thus, the clinician may not be required to access each medical imaging record to determine which records are required to diagnose the patient's current concern. As a consequence, fewer medical imaging records may be transferred from the database 112 to the clinician workstation thereby reducing strain on the network bandwidth.

In some cases, the processor 102 may receive a selection of a second condition marker from the condition list. For instance, a clinician may identify a potentially related condition and request medical imaging records related to the second condition. The processor 102 can retrieve the timeline of the condition-specific imaging records for the second condition marker from the patient dossier 118 and then display the timeline using display device 108.

Figure 3A:
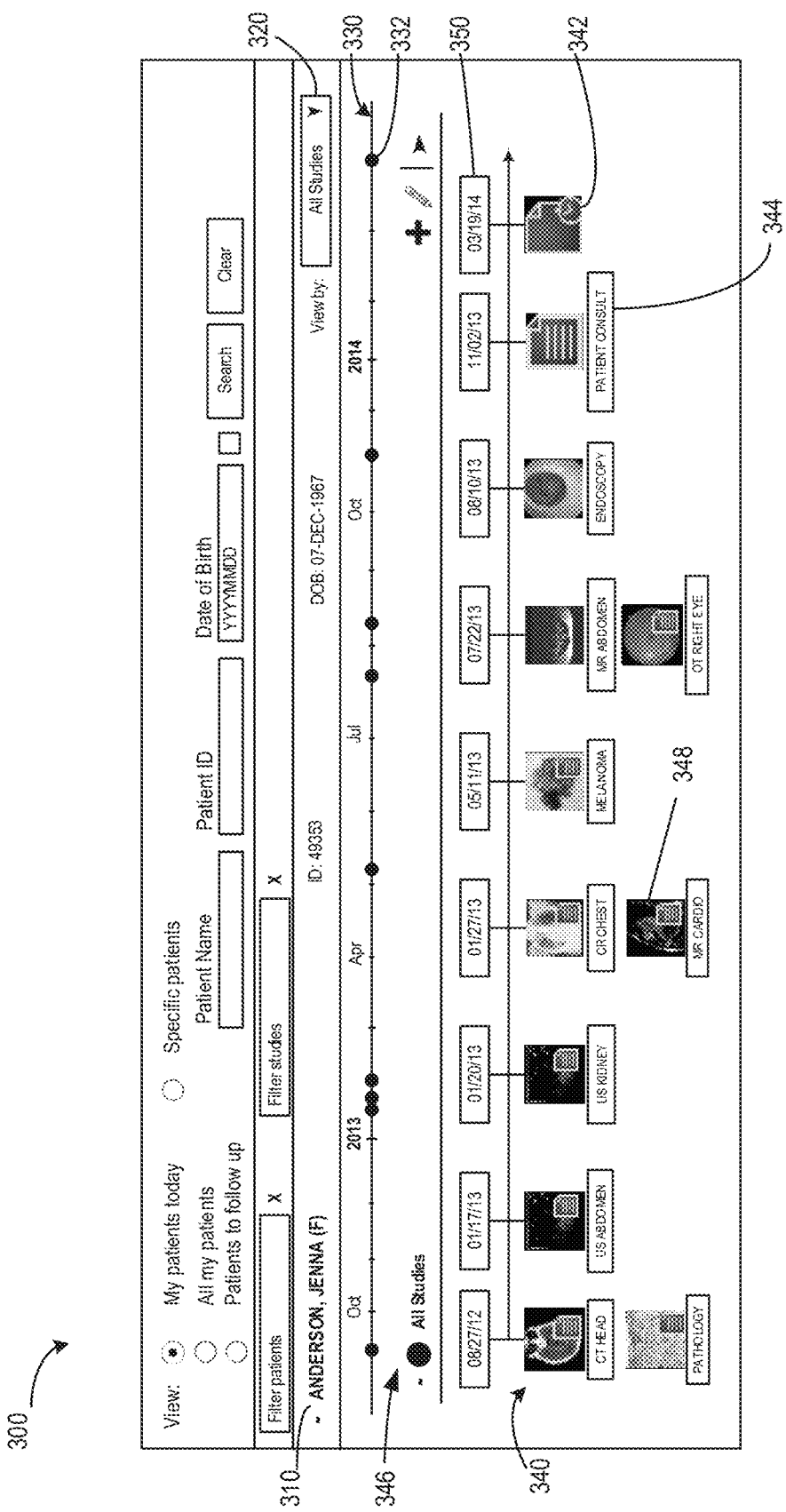
FIG. 3A is a diagram illustrating an example graphical user interface (GUI) that may be displayed to a user by the system of FIG. 1.
Figure 3B:
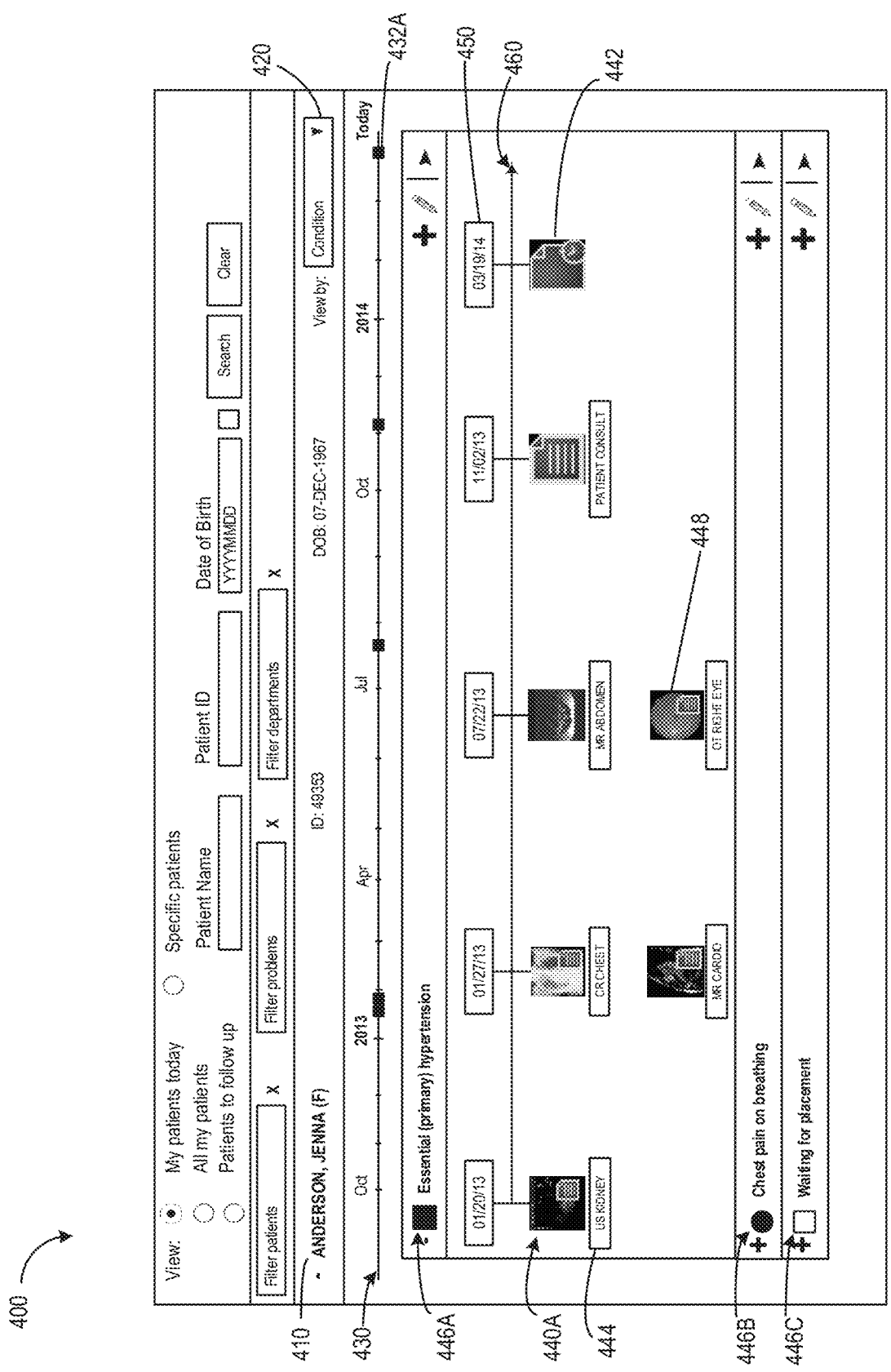
FIG. 3B is a diagram illustrating another example GUI that may be displayed to a user by the system of FIG. 1.
Figure 3C:
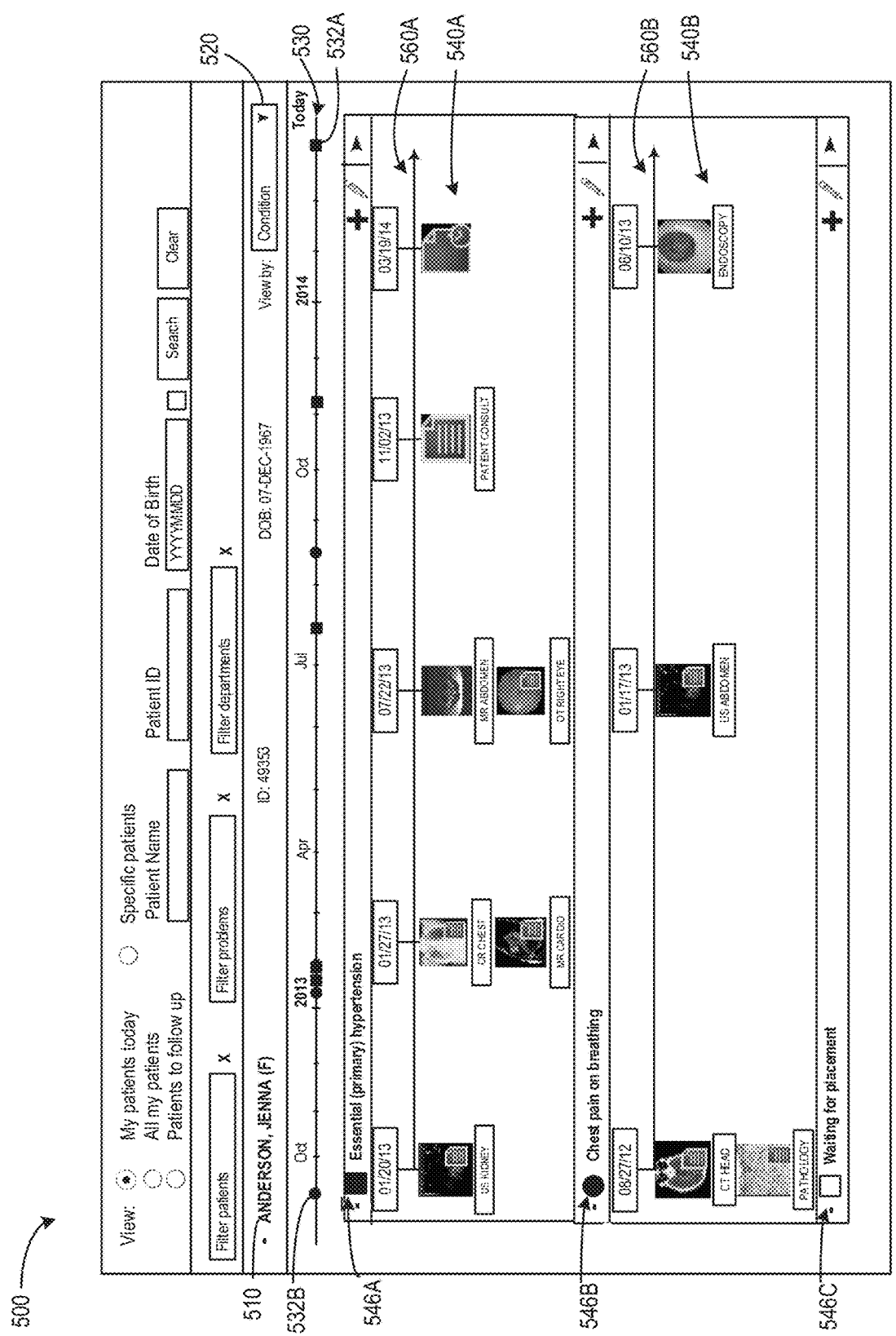
FIG. 3C is a diagram illustrating a further example GUI that may be displayed to a user by the system of FIG. 1.

In some cases, the processor 102 may generate a combined timeline of the condition-specific imaging records for the first condition marker and the condition-specific imaging records for the second condition marker (see e.g. FIG. 3C). The combined timeline can include a first condition identifier associated with each of the condition-specific imaging records for the first condition marker and a second condition identifier associated with each of the condition-specific imaging records for the second condition marker that is different from the first condition identifier. The combined timeline can then be displayed to the user separately, or in addition to, condition-specific timelines for the first and second condition markers. For instance, the combined timeline may be simplified timeline of imaging records whereas the condition-specific timelines may provide greater detail on the imaging records.

The combined timeline may provide a clinician with a simultaneous overview of the progress of multiple conditions. This may enable the clinician to identify conditions that are related, or that have potentially been misdiagnosed by identifying other related or underlying causes. The clinician may also be able to re-assign medical imaging records to more suitable condition markers based on this review.

Referring now to FIGS. 3A-3C, shown therein are examples of user interfaces that may be shown to a user of system 100.

FIG. 3A shows an example of a GUI 300 that may be displayed to a user by display device 108. The GUI 300 shows a plurality of medical imaging records 340 for a patient 310. The GUI 300 has a drop-down menu 320 indicating that all the medical imaging records for the patient 310 are currently being shown.

Each medical imaging record 340 shown in GUI 300 has an associated image record identifier 342. In general, the image record identifiers 342 shown in GUI 300 include record type identifiers 344 identifying the type of imaging record. As well, the image record identifiers 342 for the medical imaging records that are medical images include thumbnail images 348 that provide a visual indication to a user of the content of that medical imaging record 340. This may assist a clinician in more rapidly identifying relevant imaging records 340 requiring further analysis without having to access each imaging record.

The GUI 300 is an example of a medical dossier where the medical imaging records 340 for the patient 310 have yet to be arranged into condition-specific imaging records. That is, the medical imaging records 340 include imaging records for a plurality of different conditions associated with patient 310. Similarly, the imaging markers 332 on timeline 330 only provide a timeline of the imaging dates 350 of all imaging records 340.

As a result, the clinician may have to spend additional time reviewing each imaging record to determine whether they are related to the condition of interest. For instance, the clinician may be required to access and review various medical imaging records to determine if they are relevant or not. This increases the time to diagnosis for the patient, and may also increase the number of medical imaging records that must be transmitted form database 112 to the clinician workstation. The timeline 330 also merely provides an indication of when the patient has been seen, but does not differentiate between medical images for different conditions.

Referring now to FIG. 3B, shown therein is an example of a GUI 400 that may be displayed on display device 108. In GUI 400, the medical imaging records for patient 410 are shown segregated by condition. That is, the medical dossier compilation system 100 has assigned each medical imaging record 440 to a particular condition marker 446A-446C.

As shown in FIG. 3B, system 100 has received a selection of a first condition marker corresponding to essential (primary) hypertension. A timeline 430 has been generated for the first condition marker based on the imaging dates of each medical imaging record 440A assigned to the first condition marker. The timeline 430 includes first condition identifiers 432 that provide a quick visual indication to a clinician of periods when medical imaging records were acquired for the patient's primary hypertension. As well, the clinician is able to rapidly review thumbnail images 448 of many of the medical imaging records 440A to quickly identify the imaging records associated with the condition that may be helpful during the current visit with the patient.

GUI 400 also indicates that other conditions, such as condition marker 446B for chest pain on breathing are included on the patient's condition list. The clinician can select each condition marker 446 using input device 110 to display the timeline generated for that condition marker 446. In some cases, when the condition list is displayed to the user, the processor 102 may retrieve image record identifiers associated with a particular condition marker 446 from the database 112 only after that condition marker 446 has been selected. Alternatively, the processor 102 may preload image record identifiers for one or more condition marker 446 if sufficient bandwidth is available on the network.

The timeline 430 is an example of a simplified timeline of condition-specific imaging records for the condition marker 446A. The simplified timeline 430 indicates to a clinician the dates at which the patient was attended for the particular condition using the condition identifiers 432A, but does not provide much detail regarding the individual imaging records 440A acquired. In general, the simplified timeline 430 can be generated to scale to provide a clear indication of the treatment period for the patient 410. The simplified timeline 430 may highlight or emphasize for a clinician clusters or periods of greater activity related to the condition.

In some cases, the processor 102 can also generate a detailed timeline 460 of condition-specific imaging records 440A for the condition marker 446A. The detailed timeline 460 can provide additional detail regarding the condition-specific imaging records 440A. The detailed timeline 460 may not be shown to scale, but rather provides greater detail about each imaging record 440A such as a record identifier 442, record type identifier 444, and thumbnail images 448 of medical images. The detailed timeline 440A allows a clinician to rapidly review imaging records that may be potentially relevant for the patient's current visit.

Referring now to FIG. 3C, shown therein is another example GUI 500 that may be displayed on display device 108. GUI 500 generally corresponds to GUI 400 after a selection of the second condition marker 446B has been received from the user input device 110.

The processor 102 has generated a combined timeline 530 having a first condition identifier 532A corresponding to the imaging date of imaging records associated with the first condition marker and a second condition identifier 532B corresponding to the imaging date of imaging records associated with the second condition marker. The combined timeline 530 allows a clinician to review and compare the progress of imaging records 540A and 540B for condition markers 546A and 546B respectively over time.

The combined timeline 530 is another example of a simplified timeline similar to simplified timeline 430. The combined timeline 530 may highlight clusters or periods of activity for multiple conditions that are close in time or overlap. This may assist the clinician in identifying correlations or relationships between multiple conditions a patient has, and may assist in identifying the patient's underlying problems.

Detailed condition-specific timelines 560A and 560B for condition markers 546A and 546B respectively can also be displayed concurrently on GUI 500. The condition-specific timelines can again include image record identifiers such as record type and thumbnail images to allow the clinician to rapidly review the records for each condition. The condition-specific timelines 560A and 560B may not be set to the same scale, but rather are generated to provide as much detail about the individual imaging records without cluttering the GUI 500. In some cases, clinician may be able to scroll or zoom along the simplified timeline 530 and/or the detailed timelines 560 to review different time periods more closely. In some cases, the detailed timelines 560 may automatically adjust as a clinician scrolls along the simplified timeline 530 to show the details of the imaging records currently indicated on the simplified timeline 530.

The condition identifiers 532 shown in GUI 500 have different shapes to allow a clinician to easily identify when imaging records were acquired for each condition marker. Various other types of condition identifiers 532 may be used, such as different colors or patterns of identifiers. In some cases, a combined detailed timeline may also be generated (not shown). The combined detailed timeline may include details about the imaging records for multiple condition markers. These combined detailed timeline may use different identifiers to distinguish between imaging records for the various condition markers, e.g. by provided a border around each imaging record that corresponds to the condition identifier for the condition marker associated with that imaging record.

GUI 500 also includes a waiting for placement marker 546C. If a condition marker cannot be automatically identified for a particular medical imaging record by decoding module 114 or NLP module 116, then that medical imaging record may be assigned to the waiting for placement marker 546C. A clinician can select the waiting for placement marker 546C to review medical imaging records that have yet to be assigned to a condition marker. The clinician may then assign a particular medical imaging record to a condition marker using the input device 110. This allows medical imaging records that cannot be automatically analyzed for whatever reason to be easily integrated into the patient dossier 118 and associated with a condition marker.

Figure 4A:
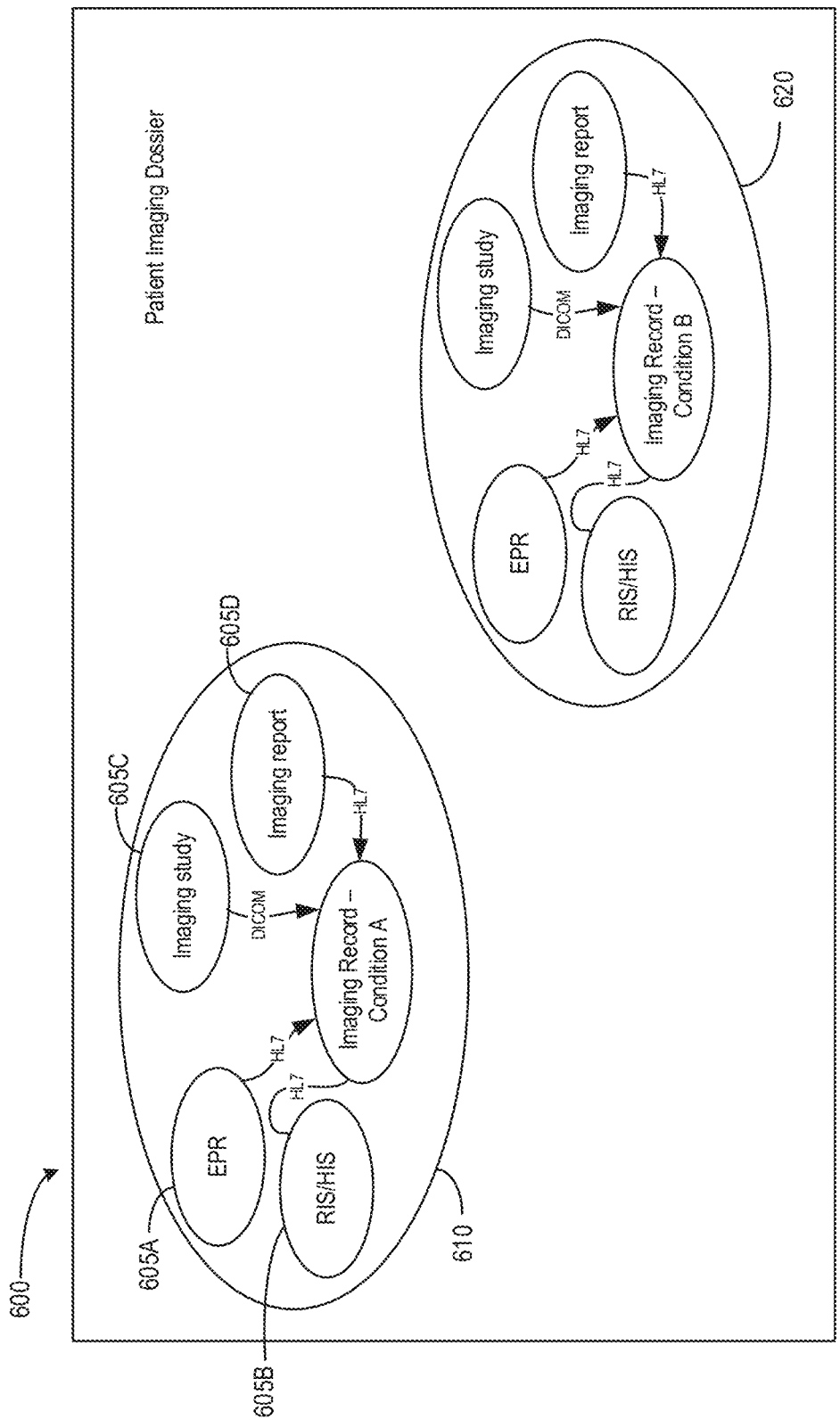
FIG. 4A is a block diagram illustrating an example of a patient imaging dossier generated by the system of FIG. 1.

Referring now to FIG. 4A, shown therein is a block diagram illustrating an example of a patient dossier 600 that includes medical imaging records 605 for various condition markers 610 and 620. The medical imaging records 605 in patient dossier 600 were associated with condition markers 610 and 620 by identifying codified condition markers in those imaging records 605. For example, the codified condition markers may have been identified using decoding module 114.

The content of the medical imaging records 605 was translated to the respective condition markers 610 by identifying codified condition markers associated with the HL7 standard (see e.g. records 605A, 605B, and 605C) and the DICOM standards (see e.g. record 605C). Various other codified condition markers may be used, including codified condition markers specific to individual institutions or organizations.

Figure 4B:
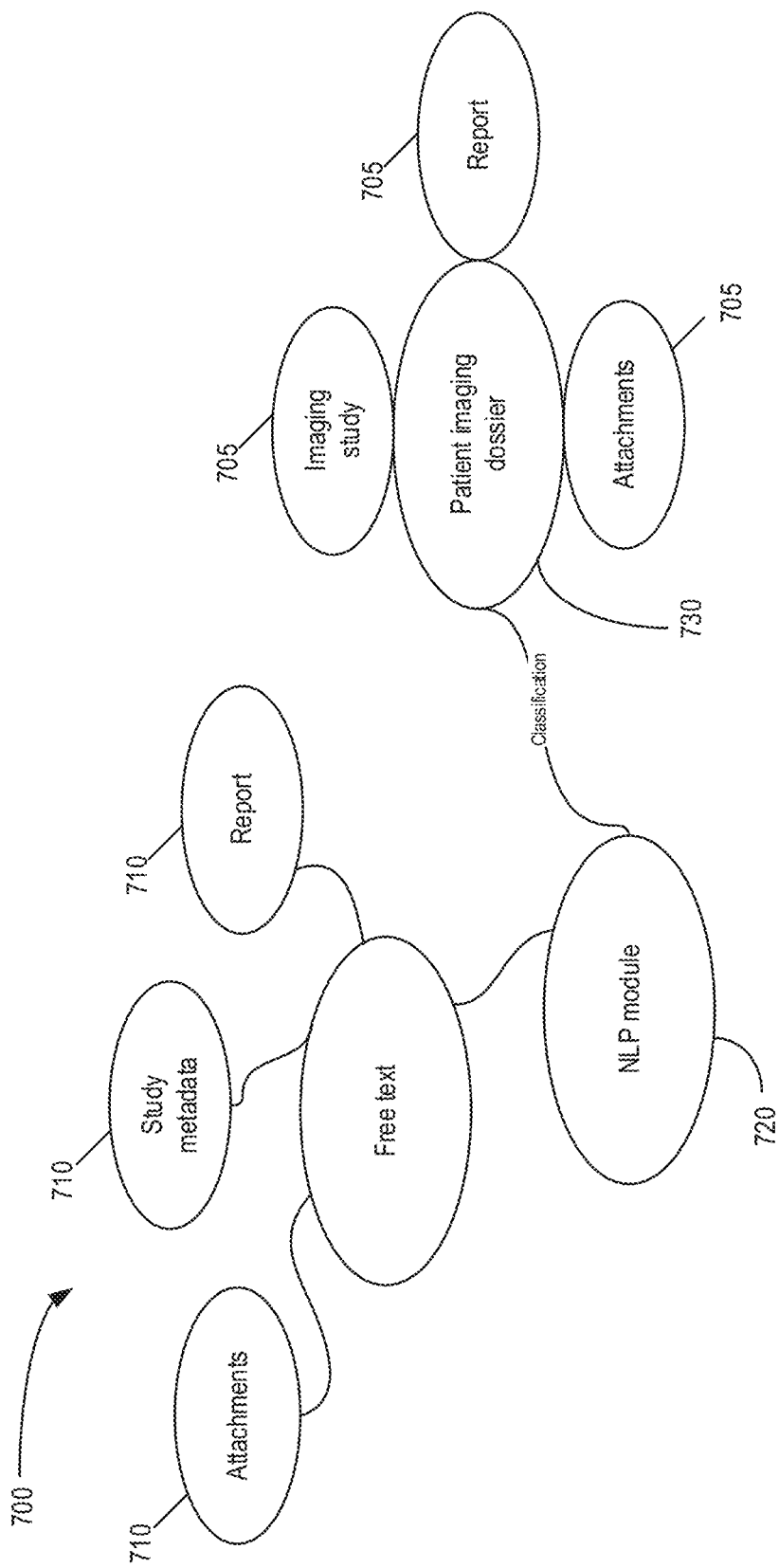
FIG. 4B is a block diagram illustrating another example of a patient imaging dossier generated by the system of FIG. 1.

Referring now to FIG. 4B is a block diagram 700 illustrating another example of a patient imaging dossier 730 generated by the system of FIG. 1. In some cases, if a codified condition marker is not identified in a medical imaging record 705, the free text of various portions 710 of the medical imaging record can be automatically analyzed to determine the condition marker associated with that imaging record.

The portions 710 of each medical imaging record 705 can be provided to an NLP module 720, such as NLP module 116. The NLP module 116 can analyze the free text content of each portion 710 of a medical imaging record 705 and identify a condition marker associated with that medical imaging record 705. The medical imaging records 705 can then be stored in the patient imaging dossier 730, assigned to the condition marker determined by the NLP module. The patient imaging dossier may also include the medical imaging records 705 in the condition-specific timelines generated as described herein above.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

The invention claimed is:

1. A method for compiling an electronic medical dossier by a client workstation comprising a processor and a user interface, the client workstation being remotely coupled to a medical imaging record database over a network, the method comprising:

receiving, by the processor, a request for a condition list for a patient from the user interface of the client workstation;

determining, by the processor, the condition list for the patient, the condition list comprising a plurality of condition markers, each condition marker representing a medical condition, wherein the plurality of condition markers includes a first condition marker and a second condition marker;

retrieving, by the client workstation, the condition list from the medical imaging record database over the network;

storing the condition list in the electronic medical dossier, the electronic medical dossier being configured to capture and log subsequent changes and updates to the condition list;

displaying the condition list in the user interface through a display device of the client workstation;

identifying, by the processor, a plurality of medical imaging records for the patient stored in the medical imaging record database, each medical imaging record having at least one medical image and an imaging date, and each medical imaging record being associated with a particular instance of an imaging procedure;

determining, by the processor, at least one condition-specific imaging record for each of the first condition marker and the second condition marker by assigning each medical imaging record in the plurality of medical imaging records to one of the condition markers in the condition list;

generating, by the processor, a plurality of thumbnail images comprising a thumbnail image for each of the at least one condition-specific imaging record for each of the first condition marker and the second condition marker, each thumbnail image being a reduced-data-size version of the at least one medical image corresponding to the at least one condition-specific imaging record;

generating, by the processor, a timeline of condition-specific imaging records for each of the first condition marker and the second condition marker using the imaging date of the condition-specific imaging records for the first condition marker and the second condition marker, wherein each timeline of condition-specific imaging records defines a sequence of at least art of the plurality of thumbnail images corresponding to each of the at least one condition-specific imaging for the first condition marker and second condition marker, each thumbnail image is positioned in the corresponding sequence based on the imaging date corresponding to the condition-specific imaging record corresponding to that thumbnail image, and the timeline of condition-specific imaging records for each of the first condition marker and the second condition marker includes medical imaging records associated with a plurality of separate instances of imaging procedures;

storing the timeline of condition-specific imaging records for each of the first condition marker and the second condition marker in the electronic medical dossier;

receiving, by the processor, a selection of the first condition marker in the displayed condition list from the user interface of the client workstation;

retrieving, by the processor, from the electronic medical dossier, in response to the receiving the selection of the first condition marker, the timeline of the condition-specific imaging records for the first condition marker;

receiving, by the processor, a selection of the second condition marker in the displayed condition list from the user interface of the client workstation;

retrieving, by the processor, from the electronic medical dossier, in response to receiving the selection of the second condition marker, the timeline of the condition-specific imaging records for the second condition marker;

displaying both the timeline of the condition-specific imaging records for the first condition marker and the timeline of the condition-specific imaging records for the second condition marker concurrently on the display device of the client workstation;

receiving, by the processor, a selection of a particular thumbnail image corresponding to a particular condition-specific imaging record from the user interface of the client workstation; and retrieving by the client workstation, the particular condition-specific imaging record from the medical imaging record database over the network.

2. The method of claim 1, further comprising:

generating, by the processor, a combined timeline of the condition-specific imaging records for the first condition marker and the condition-specific imaging records for the second condition marker;

wherein the combined timeline includes a first condition identifier associated with each of the condition-specific imaging records for the first condition marker and a second condition identifier associated with each of the condition-specific imaging records for the second condition marker, the second condition identifier being different than the first condition identifier.

3. The method of claim 1, wherein for the at least one medical imaging record, that medical imaging record is assigned to the condition marker by:

determining, by the processor, if a codified condition marker is present in that medical imaging record, the codified condition marker corresponding to a national and/or international standard encoding or an institution-specific encoding of a particular condition marker in the condition list; and if the codified condition marker is present:

translating, by the processor, the codified condition marker into the corresponding condition marker in the condition list, thereby generating a translated condition marker; and assigning, by the processor, that medical imaging record to the translated condition marker.

4. The method of claim 3, further comprising:

if the codified condition marker is not present:

identifying, by the processor, the condition marker using natural language processing by analyzing a free text portion of the medical imaging record; and assigning that medical imaging record to the identified condition marker.

5. The method of claim 3, further comprising:

if the codified condition marker is not present;

displaying each of the at least one medical imaging record on the display device;

receiving, by the processor, a user-selected condition marker from the user interface for each of the at least one medical imaging record; and assigning, by the processor, each medical imaging record in the at least one medical imaging record to the user-selected condition marker for that medical imaging record.

6. The method of claim 1, further comprising:

displaying the condition list through the user interface on the display device; and receiving, by the processor, the selection of the first condition marker from the user interface in response to the displayed condition list.

7. A system for compiling an electronic medical dossier, the system comprising:

a medical imaging record database for storing a plurality of medical imagine records;

a client workstation having a user interface and display device, wherein the client workstation is remotely coupled to the medical imaging record database over a network; and a processor coupled to the medical imaging record database over the network and to the user interface, the processor configured to:

receive, a request for a condition list for a patient from the user interface of the client workstation;

determine the condition list for the patient, the condition list comprising a plurality of condition markers, each condition marker representing a medical condition, wherein the plurality of condition markers includes a first condition marker and a second condition marker;

retrieve the condition list from the medical imaging record database over the network;

store the condition list in the electronic medical dossier, the electronic medical dossier being configured to capture and log subsequent changes and updates to the condition list;

display the condition list in the user interface through the display device of the client workstation;

identify a plurality of medical imaging records for the patient stored in the medical imaging record database, each medical imaging record having at least one medical image and an imaging date, and each medical imaging record being associated with a particular instance of an imaging procedure;

determine at least one condition-specific imaging record for each of the first condition marker and the second condition marker by assigning each medical imaging record in the plurality of medical imaging records to one of the condition markers in the condition list;

generate a plurality of thumbnail images comprising a thumbnail image for each of the at least one condition-specific imaging record for each of the first condition marker and the second condition marker, each thumbnail image being a reduced-data-size version of the at least one medical image corresponding to the at least one condition-specific imaging record;

generate a timeline of condition-specific imaging records for each of the first condition marker and the second condition marker using the imaging date of the condition-specific imaging records for the first condition marker and the second condition marker, wherein each timeline of condition-specific imaging records defines a sequence of at least part of the plurality of thumbnail images corresponding to each of the at least one condition-specific imaging record for the first condition marker and the second condition marker, each thumbnail image is positioned in the corresponding sequence based on the imaging date corresponding to the condition-specific imaging record corresponding to that thumbnail image, and the timeline of condition-specific imaging records for each of the first condition marker and the second condition marker includes medical imaging records associated with a plurality of separate instances of imaging procedures;

store the timeline of condition-specific imaging records for each of the first condition marker and the second condition marker in the electronic medical dossier;

receive a selection of the first condition marker in the displayed condition list from the user interface of the client workstation;

retrieve, from the electronic medical dossier, in response to receiving the selection of the first condition marker the timeline of the condition-specific imaging records for the first condition marker;

receive a selection of the second condition marker in the displayed condition list from the user interface of the client workstation;

retrieve, from the electronic medical dossier, in response to the receiving the selection of the second condition marker, the timeline of the condition-specific imaging records for the second condition marker;

display both the timeline of the condition-specific imaging records for the first condition marker and the timeline of the condition-specific imaging records for the second condition marker concurrently on the display device of the client workstation;

receive a selection of a particular thumbnail image corresponding to a particular condition-specific imaging record from the user interface of the client workstation; and retrieve the particular condition-specific imaging record from the medical imaging record database over the network.

8. The system of claim 7, wherein the processor is further configured to:
generate a combined timeline of the condition-specific imaging records for the first condition marker and the condition-specific imaging records for the second condition marker, the combined timeline including a first condition identifier associated with each of the condition-specific imaging records for the first condition marker and a second condition identifier associated with each of the condition-specific imaging records for the second condition marker, the second condition identifier being different than the first condition identifier.

9. The system of claim 7, wherein, for the at least one medical imaging record, the processor is configured to assign that medical imaging record to the condition marker by:
determining if a codified condition marker is present in that medical imaging record, the codified condition marker corresponding to a national and/or international standard encoding or an institution-specific encoding of a particular condition marker in the condition list; and
if the codified condition marker is present:
translating the codified condition marker into the corresponding condition marker in the condition list, thereby generating a translated condition marker; and
assigning that medical imaging record to the translated condition marker.

10. The system of claim 9, wherein the processor is further configured to:
if the codified condition marker is not present:
identify the condition marker using natural language processing by analyzing a free text portion of the medical imaging record; and
assign that medical imaging record to the identified condition marker.

11. The system of claim 9, wherein the processor is further configured to:
if the codified condition marker is not present;
display each of the at least one medical imaging record using the display device;
receive a user-selected condition marker from the user input device for each of the at least one medical imaging record; and assign each medical imaging record in the at least one medical imaging record to the user-selected condition marker for that medical imaging record.

12. The system of claim 7, wherein the processor is further configured to:
display the condition list using the display device; and
receive the selection of the first condition marker from the user input device in response to the displayed condition list.

13. A method for compiling an electronic medical dossier by a client workstation comprising a processor and a user interface, the client workstation being remotely coupled to a medical imaging record database over a network, the method comprising:
receiving, by the processor, a request for a condition list for a patient from the user interface of the client workstation;
determining, by the processor, the condition list for the patient, the condition list comprising a plurality of condition markers, each condition marker representing a medical condition, wherein the plurality of condition markers includes a first condition marker;
retrieving, by the client workstation, the condition list from the medical imaging record database over the network;
storing the condition list in the electronic medical dossier, the electronic medical dossier being configured to capture and log subsequent changes and updates to the condition list;
displaying the condition list in the user interface through a display device of the client workstation;
identifying, by the processor, a plurality of medical imaging records for the patient stored in the medical imaging record database, each medical imaging record having at least one medical image and an imaging date, and each medical imaging record being associated with a particular instance of an imaging procedure;
determining, by the processor, at least one condition-specific imaging record for the first condition marker by assigning each medical imaging record in the plurality of medical imaging records to one of the condition markers in the condition list;
generating, by the processor, a plurality of thumbnail images comprising a thumbnail image for each of the at least one condition-specific imaging record for the first condition marker, each thumbnail image being a reduced-data-size version of the at least one medical image corresponding to the at least one condition-specific imaging record;
generating, by the processor, a timeline of condition-specific imaging records for the first condition marker using the imaging date of the condition-specific imaging records for the first condition marker, wherein the timeline of condition-specific imaging records defines a sequence of at least part of the plurality of thumbnail images corresponding to each of the at least one condition-specific imaging records for the first condition marker, each thumbnail image is positioned in the corresponding sequence based on the imaging date corresponding to the condition-specific imaging records corresponding to that thumbnail image, and the timeline of condition-specific imaging records for the first condition marker includes medical imaging records associated with a plurality of separate instances of imaging procedures;

storing the timeline of condition-specific imaging records for the first condition marker in the electronic medical dossier;

receiving, by the processor, a selection of the first condition marker in the displayed condition list from the user interface of the client workstation;

retrieving, by the processor, from the electronic medical dossier, in response to the receiving the selection of the first condition marker, the timeline of the condition-specific imaging records for the first condition marker;

displaying the timeline of the condition-specific imaging records for the first condition marker on the display device of the client workstation;

receiving, by the processor, a selection of a particular thumbnail image corresponding to a particular condition-specific imaging record from the user interface of the client workstation; and retrieving, by the client workstation, the particular condition-specific imaging record from the medical imaging record database over the network.

14. The method of claim 13, wherein for the at least one medical imaging record, that medical imaging record is assigned to the condition marker by:

determining, by the processor, if a codified condition marker is present in that medical imaging record, the codified condition marker corresponding to a national and/or international standard encoding or an institution-specific encoding of a particular condition marker in the condition list; and if the codified condition marker is present:
translating, by the processor, the codified condition marker into the corresponding condition marker in the condition list, thereby
generating a translated condition marker; and
assigning, by the processor, that medical imaging record to the translated condition marker.

15. The method of claim 14, further comprising:
if the codified condition marker is not present:
identifying, by the processor, the condition marker using natural language processing by analyzing a free text portion of the medical imaging record; and
assigning that medical imaging record to the identified condition marker.

16. The method of claim 14, further comprising:
if the codified condition marker is not presents:
displaying each of the at least one medical imaging record on the display device;
receiving, by the processor, a user-selected condition marker from the user interface for each of the at least one medical imaging record; and
assigning, by the processor, each medical imaging record in the at least one medical imaging record to the user-selected condition marker for that medical imaging record.

17. The method of claim 13, further comprising:
displaying the condition list through the user interface on the display device; and
receiving, by the processor, the selection of the first condition marker from the user interface in response to the displayed condition list.

* * * * *

UNITED STATES PATENT AND TRADEMARK OFFICE
CERTIFICATE OF CORRECTION

PATENT NO. : 10,949,501 B2
APPLICATION NO. : 14/845832
DATED : March 16, 2021
INVENTOR(S) : Dobrean Page 1 of 1

It is certified that error appears in the above-identified patent and that said Letters Patent is hereby corrected as shown below:

In the Claims

Column 16, Claim 1, Line 33: "art" should read -- part --.

Column 16, Claim 1, Line 35: "imaging for" should read -- imaging record for --.

Column 16, Claim 1, Line 36: "and second" should read -- and the second --.

Column 17, Claim 7, Line 63: "imagine" should read -- imaging --.

Column 20, Claim 13, Line 59: "records" should read -- record --.

Column 20, Claim 13, Line 63: "records" should read -- record --.

Signed and Sealed this
Twenty-sixth Day of April, 2022

Katherine Kelly Vidal
*Director of the United States Patent and Trademark Office*